United States Patent
Salter et al.

(10) Patent No.: US 6,631,721 B1
(45) Date of Patent: *Oct. 14, 2003

(54) NEBULIZER MOUTHPIECE AND ACCESSORIES

(75) Inventors: Peter W. Salter, Tehachapi, CA (US); James Chua, Bakersfield, CA (US); Walter Van Horn, Arvin, CA (US); Duane D. Kazal, Tehachapi, CA (US); Laurence McGann, Woodland, CA (US)

(73) Assignee: Salter Labs, Arvin, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/831,042
(22) PCT Filed: Nov. 3, 1999
(86) PCT No.: PCT/US99/25828
§ 371 (c)(1), (2), (4) Date: May 3, 2001
(87) PCT Pub. No.: WO00/27455
PCT Pub. Date: May 18, 2000

Related U.S. Application Data
(60) Provisional application No. 60/107,436, filed on Nov. 6, 1998.

(51) Int. Cl.[7] .............................................. A61M 11/00
(52) U.S. Cl. .............................. 128/230.21; 128/203.1; 128/207.14; 128/863
(58) Field of Search ....................... 128/200.17, 200.18, 128/200.21, 200.23, 203.12, 203.16, 203.23, 204.14, 207.14, 863

(56) References Cited

U.S. PATENT DOCUMENTS

| 3,363,260 A | | 1/1968 | Garbe | |
|---|---|---|---|---|
| 3,630,196 A | | 12/1971 | Bird | |
| 3,664,337 A | * | 5/1972 | Lindsey et al. | 128/200.21 |
| 3,769,973 A | | 11/1973 | Esbenshade, Jr. | |
| 3,826,255 A | * | 7/1974 | Havstad et al. | 128/200.21 |
| 3,874,379 A | * | 4/1975 | Enfield et al. | 128/200.21 |
| 3,903,884 A | * | 9/1975 | Huston et al. | 128/200.21 |
| 3,933,171 A | | 1/1976 | Hay | |

(List continued on next page.)

FOREIGN PATENT DOCUMENTS

| EP | 0281650 A1 | * | 9/1988 | 128/200.14 |
|---|---|---|---|---|
| WO | WO 86/01731 | | 3/1986 | |

Primary Examiner—Weilun Lo
Assistant Examiner—Joseph F. Weiss
(74) Attorney, Agent, or Firm—Davis & Bujold, P.L.L.C.

(57) ABSTRACT

This invention is a device (10) for inspiration of a mist from a nebulizer, the device comprising an inlet connector (12, 32) adapted to engage an outlet port of a nebulizer; a hollow mouthpiece element (126, 34) for insertion into a patient's mouth; a conduit (14) forming a fluid connection between the inlet connector, and the hollow mouthpiece element; an exhaust valve (26) for removing expiratory gases which are exhaled into the mouthpiece element to the ambient atmosphere via the exhaust/positive expiratory pressure (PEP) valve (26, 50) positioned on the conduit between the inlet connector, and the mouthpiece element; and a filter housing (44) containing a filter (60) for filtering the exhaled gases passing from the exhaust/PEP valve.

4 Claims, 10 Drawing Sheets

U.S. PATENT DOCUMENTS

| | | |
|---|---|---|
| 3,993,050 A | 11/1976 | Robinson et al. |
| 4,062,358 A | 12/1977 | Kritzer |
| 4,158,360 A | 6/1979 | Adams |
| 4,207,884 A | 6/1980 | Isaacson |
| 4,221,381 A | 9/1980 | Ericson |
| 4,232,683 A | 11/1980 | Bartholomew et al. |
| 4,259,951 A | 4/1981 | Chernack et al. |
| 4,403,616 A | 9/1983 | King |
| 4,421,120 A | 12/1983 | Edwards, Jr. et al. |
| 4,446,863 A | 5/1984 | Rubin et al. |
| 4,452,239 A | 6/1984 | Malem |
| 4,533,137 A | 8/1985 | Sonne |
| 4,601,465 A | 7/1986 | Roy |
| 4,620,648 A | 11/1986 | Schwartzman |
| 4,706,685 A | 11/1987 | Jones, Jr. et al. |
| 4,736,750 A | 4/1988 | Valdespino et al. |
| 4,768,520 A | 9/1988 | Varraux et al. |
| 4,944,306 A | 7/1990 | Alvino |
| 4,973,047 A | 11/1990 | Norell |
| 5,020,530 A | 6/1991 | Miller |
| 5,027,809 A * | 7/1991 | Robinson ............... 128/203.24 |
| 5,320,107 A | 6/1994 | O'Brien |
| 5,388,571 A | 2/1995 | Roberts et al. |
| 5,451,190 A | 9/1995 | Liardet |
| 5,479,920 A * | 1/1996 | Piper et al. ............ 128/204.23 |
| 5,522,380 A | 6/1996 | Dwork |
| 5,584,285 A | 12/1996 | Salter et al. |
| 5,598,839 A | 2/1997 | Niles et al. |
| 5,727,542 A | 3/1998 | King |
| 6,176,234 B1 * | 1/2001 | Salter et al. ............ 128/200.18 |

\* cited by examiner

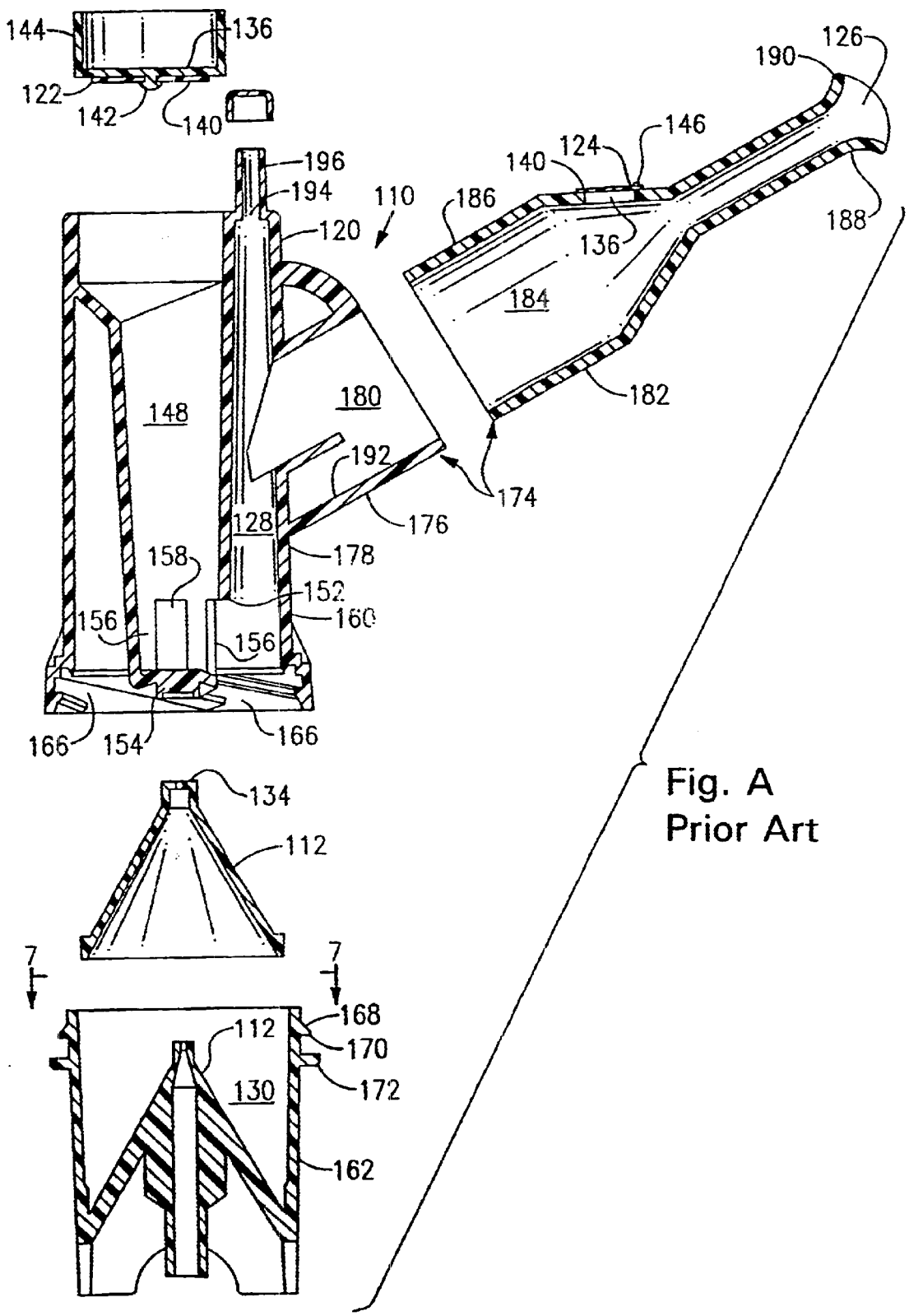
Fig. A
Prior Art

US 6,631,721 B1

NEBULIZER MOUTHPIECE AND ACCESSORIES

This application claims the benefit of provisional application Ser. No. 60/107,436 filed Nov. 6, 1998.

BACKGROUND OF THE INVENTION

This invention relates to an improved nebulizer mouthpiece and accessories.

DESCRIPTION OF THE PREVIOUSLY PUBLISHED ART

Our earlier U.S. Pat. No. 5,584,285, discloses a nebulizer with a mouthpiece having a flap valve 124 shown in FIG. 3 of the patent which is reproduced here as FIG. A. When the patient exhales into the mouthpiece 126 the air pressure causes the flap 124 to open and let the exhaust air out of the mouthpiece.

This early design, while operational and commercially effective, is not optimal. Since the flap valve 124 is in the path of the incoming inspiration mist, there is the possibility that the mist under sufficient pressure can cause the flap to slightly open such that some of the mist will leave the mouthpiece in the form of rainout before it reaches the patient. When the patient exhales, there is no structure to direct the exhaust flow against the valve or increase back pressure to assist the valve opening. The valve only opens when the exhaust gas back pressure reaches a certain level. The flap valve is made of a stiff yet flexible material and thus it will inherently have some resistance to opening at very low pressures. If any rainout accumulates on the external surface of the flap valve, it is also difficult for the liquid material to flow back into the mouthpiece. The inner peripheral surface of the flap may stick to the overlapping external surface of the mouthpiece when the inner surface of the flap is wet.

OBJECTS OF THE INVENTION

It is an object of this invention to provide an improved mouthpiece exhalation valve for a nebulizer or breathing circuit containing a nebulizer where the design of the internal passageway contains an offset which causes the inspiration mist flow to bypass the exhaust valve without impingement together with a filter arrangement associated with the exhaust valve and a positive expiratory pressure valve and/or a positive expiratory pressure (PEP) valve.

SUMMARY OF THE INVENTION

According to the invention there is provided a mouthpiece device for inspiration of a mist from a nebulizer comprising: an inlet connector adapted to engage the outlet port of a nebulizer; a hollow mouthpiece element for insertion into a patient's mouth, a conduit forming a fluid connection between the inlet connector and the hollow mouthpiece element; an exhaust valve for removing exhalation gases which are exhaled into the mouthpiece element to outside the device, said exhaust valve being positioned on the conduit between the inlet connector and the mouthpiece element; and a filter housing incorporating a filter to filter exhaled gases passing from the exhaust valve.

Also according to the invention there is provided a mouthpiece device for inspiration of a mist from a nebulizer comprising: an inlet connector adapted to engage the outlet port of a nebulizer; a hollow mouthpiece element for insertion into a patient's mouth, a conduit forming a fluid connection between the inlet connector and the hollow mouthpiece element; an exhaust valve for removing exhalation gases which are exhaled into the mouthpiece element to outside the device, said exhaust valve being positioned on the conduit between the inlet connector and the mouthpiece element; and a positive expiratory pressure valve is disposed to produce a back pressure in the gases exhaled through the exhaust valve.

Also according to the invention, there is provided a mouthpiece device for inspiration of a mist from a nebulizer comprising: an inlet connector adapted to engage the outlet port of a nebulizer; a hollow mouthpiece element for insertion into a patient's mouth, a conduit forming a fluid connection between the inlet connector and the hollow mouthpiece element; an exhaust outlet for removing exhalation gases which are exhaled into the mouthpiece element to outside the device, said exhaust outlet being positioned on the conduit between the inlet connector and the mouthpiece element; and a positive expiratory pressure valve is disposed to produce a back pressure in the gases exhaled through the exhaust outlet.

Also according to the invention there is provided a method for breathing an inspiration of a mist from a nebulizer comprising: using a mouthpiece element having an inlet connector adapted to engage the outlet port of a nebulizer; a hollow mouthpiece element for insertion into a patient's mouth; a conduit forming a fluid connection between the inlet connector and the hollow mouthpiece element; an exhaust valve positioned on the conduit between the inlet connector and the mouthpiece element for removing exhalation gases which are exhaled into the mouthpiece element to outside the device; and a filter housing incorporating a filter to filter exhaled gases passing from the exhaust valve.

BRIEF DESCRIPTION OF THE DRAWINGS

The invention will now be described, by way of example, with reference to the accompanying drawings, in which:

FIG. A is a portion of an exploded side view in cross-section of a prior published mouthpiece and a portion of the nebulizer.

FIG. 1 is an exploded perspective view of the mouthpiece with the valve disc and retainer ring;

FIG. 2 is a cross-sectional side view of the mouthpiece;

FIG. 3 is a top view of a suitable valve disc with peripheral and radial cuts;

FIG. 4 is a side view of the mouthpiece without the retaining ring;

FIG. 5 is a top view of the mouthpiece without the retaining ring and valve disc;

FIGS. 6*a*, 6*b*, 6*c*, 6*d* illustrate various cut patterns for the valve disc;

FIGS. 7*a* and 7*b* illustrate alternative valve support embodiments;

FIG. 8 is an exploded side view of the mouthpiece with a partially threaded valve body and optional filter and/or an adjustable positive expiratory pressure (PEP) valve with manometer connector;

FIG. 9 is a sectional side elevation of the optional PEP valve shown in FIG. 8;

FIG. 10 is a top view of the PEP valve shown in FIG. 9;

FIG. 11 is an perspective view from the top of the filter body shown in FIG. 8;

FIG. 12 is a rear perspective view of the filter body shown in FIGS. 8 and 11;

FIG. 13 is an perspective view from the bottom of the filter body shown in FIGS. 8, 11, and 12;

FIG, 14 is a partial cross-sectional front elevation of the filter body showing a filter located in place for use;

DESCRIPTION OF THE PREFERRED EMBODIMENTS

Figure 1:
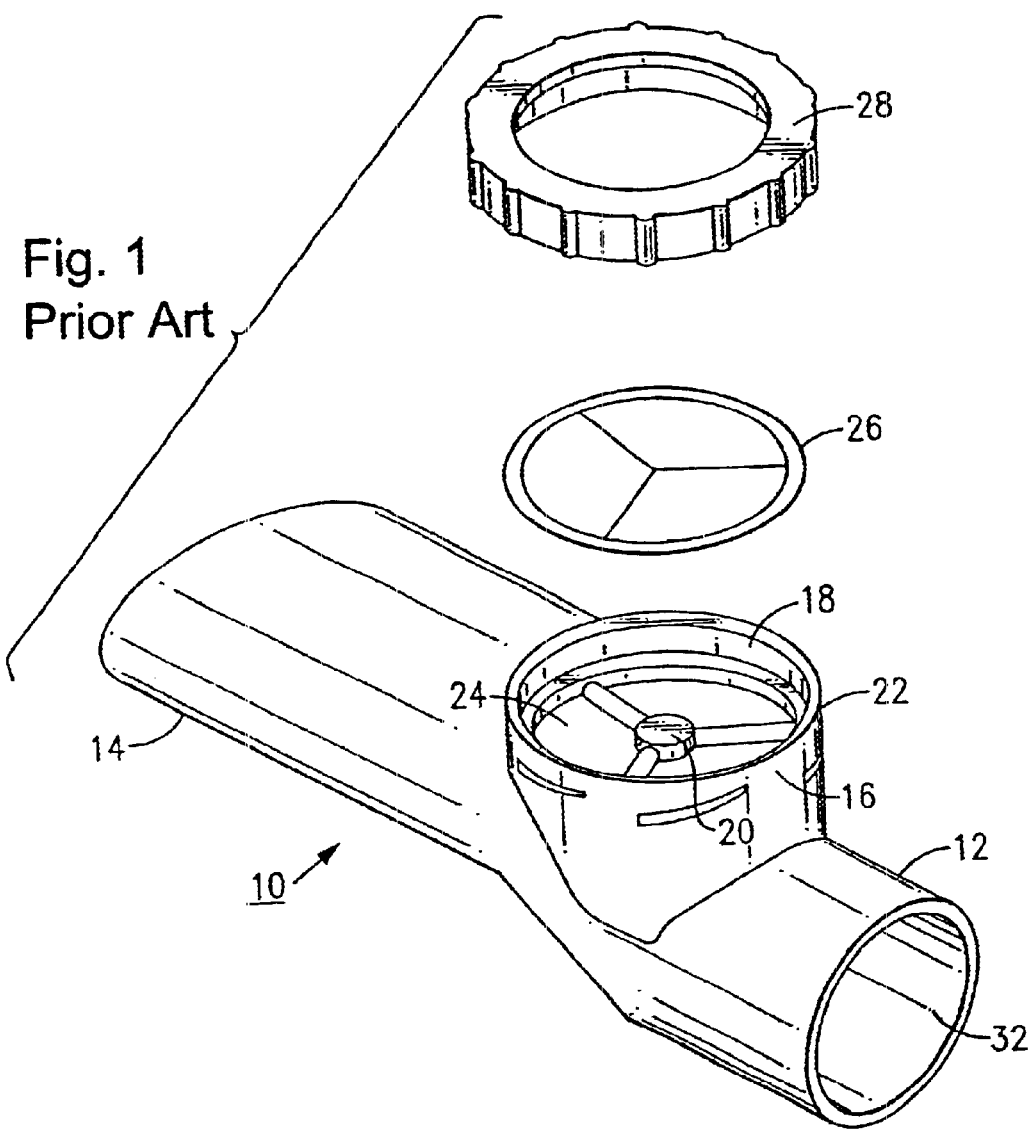

The improved mouthpiece according to the invention will now be described by referring to FIGS. 1–7. The mouthpiece 10 has a circular connector piece 12 which engages the outlet of a nebulizer in the same way that the mouthpiece engages the nebulizer in FIG. A. The opposite end of this mouthpiece device is the mouth shaped end piece 14 that, in use, is placed in the patient's mouth. On top is a valve disc housing 16 that holds the exhaust valve for exhausting the exhalation from a patient. In the exploded view of FIG. 1, the valve housing 16 contains an inner ring 18 the base which serves as a support ring for the valve disc. In the embodiment illustrated there is a central hub 20 which is supported by three arms 22. These arms are quite thin so that the open areas 24 between them represent a substantial portion of the cross-sectional area in the housing. Other configurations and different numbers of arms can be used. Above the housing in the exploded view is the valve disc 26 sized fit on top of the arms and the support ring 18. The arms 22 and hub 20 prevent the valve disc 26 from opening inwardly during inhalation. Above the valve disc in the exploded view is a retainer ring 28 having the outer wall shown and an inner wall (not shown) which is of slightly smaller diameter. The outer wall screw threads over threads 30 of the valve housing wall 16 to hold the outer peripheral area of the valve disc in place, by means of the inner wall, when the unit is assembled. The retaining ring 28 has a series of projections or ribs to facilitate gripping the ring and twisting it off the threads 30 for removal.

Figure 2:
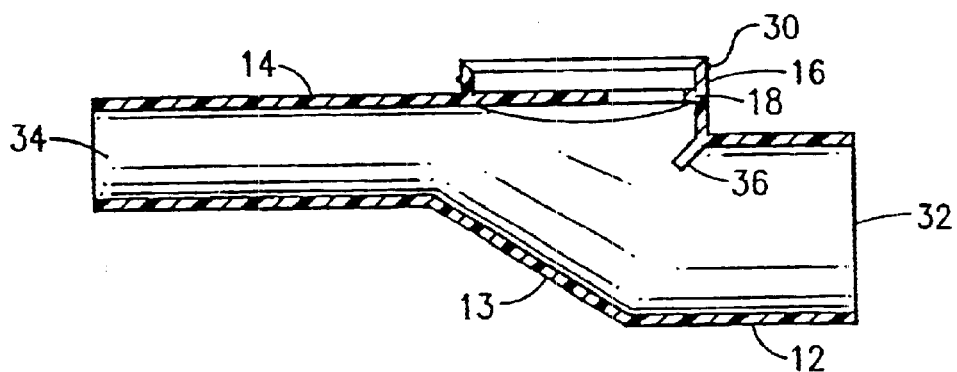

FIG. 2 is a cross-sectional side view of the mouthpiece device showing the elevational relationship of the parts and passageways. For greater clarity, the retaining ring 28 and the valve disc have been removed. The circular connector 12 will fit into the conventional circular outlet port of nebulizer. The mouth shaped end piece 14 at the other end is positioned above the center line of the circular connector 12. The back wall 13 of the connector 12 joins the connector to the upper mouthpiece. The valve housing 16 is part of the mouth shaped end piece 14. Inside the housing the support ring 18 together with the hub 20 and support arms 22 are arranged to support the valve disc 26.

When the mouthpiece is used by a patient, inspiration mist enters the circular connector 12 through its opening 32 and passes through the device and out the opening 34 in the mouthpiece. In that flow path inside the circular connector 12 is a deflector 36 which extends out at an obtuse angle from the inside wall of the circular connector 12 toward opening 34. The purpose of the deflector is two fold. First, with regard to the incoming inspiration mist, the deflector deflects that gas stream away from the valve disc in the valve housing so that the mist will not strike the valve disc and thus there is no possibility that some of the mist might leave through the valve disc. The second function is that in the respiration cycle when the patient is exhaling, the exhalation gas will be deflected so that exhalation gas is directed into the valve housing 16 where it can exhaust through the valve disc 26.

Figure 3:
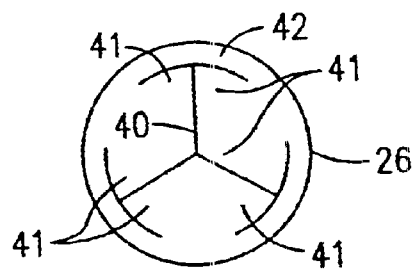

FIG. 3 is a top view of the thin valve disc 26. The radial cuts 40 and annular cuts 42 in the valve disc facilitate draining the accumulated moisture back into the mouthpiece on inhalation. There can be many possible cut patterns in the disc to define various flaps which will open upwardly when the exhalation pressure is applied to permit the exhalation gas to leave the mouthpiece. Seen here are three radial cuts 40 from the center and three annular cuts 42 which define six flaps 41. As exhalation gas pressure is applied from below, these flaps will open along the cut lines to let gas escape from the mouthpiece.

Figure 4:
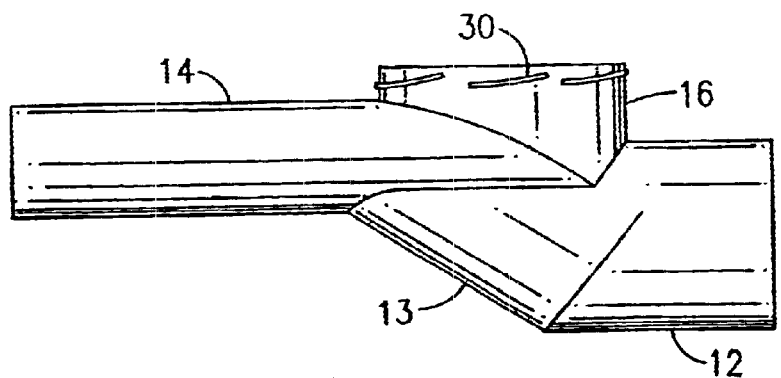
Figure 6A:
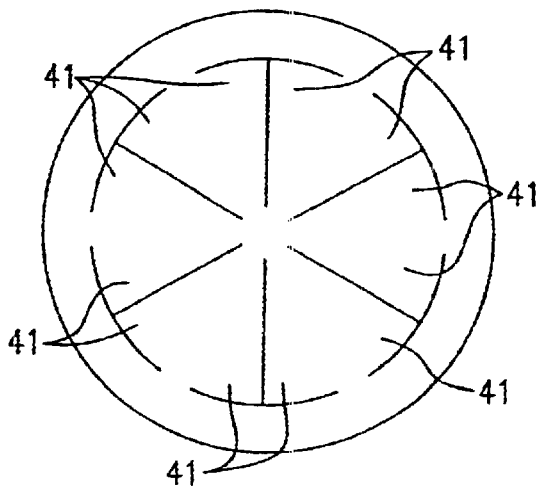
Figure 6B:
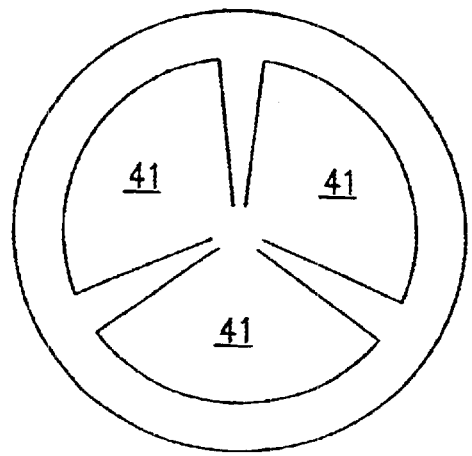
Figure 6C:
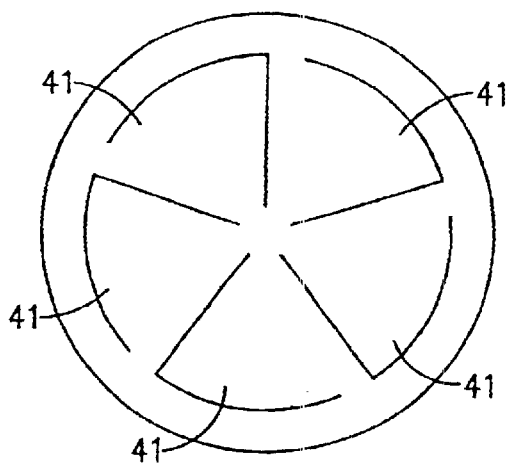
Figure 6D:
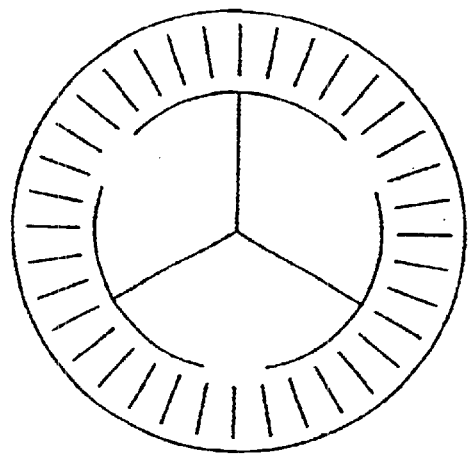

FIG. 4 is an outside view of the device showing again the elevational relationship between the circular connector 12, its back wall 13 connecting to the higher level mouth shaped end piece 14. The valve housing is made a part of the mouth shaped end piece 16 above where it connects to the circular connector.

Figure 5:
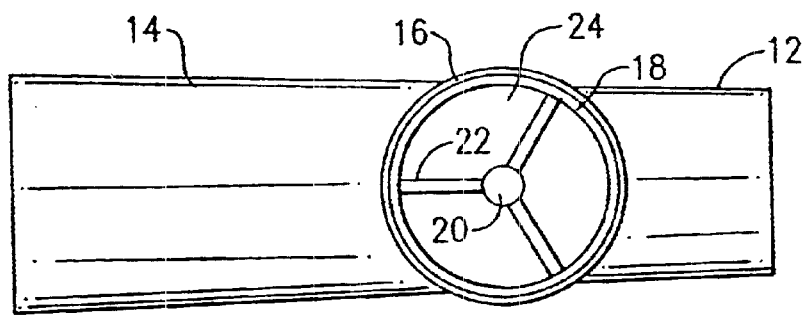

FIG. 5 is a top view of the device without the retaining ring 28 and valve disc 26. The support structure for the valve disc 26 is made up of the ring surface 18, the three grille arms 22 and the central hub 20. The end of the mouth shaped piece that is placed in the patient's mouth has a greater width than the opposite end where the valve housing is located. The mouth end has an oval opening to better anatomically fit in the patient's mouth.

FIGS. 6a–d illustrate various cut patterns for the valve disc 26. In 6a, each of six radial cuts the center form a flap 41 on either side of the cut in conjunction with annular cuts so as to provide twelve flaps which can open up in response to the exhalation pressure. In 6b there are three large flaps 41 which pivot adjacent the disc center and extend toward the periphery. In 6c where each radial cut meets the annular cut it forms the apex for a flap. Thus here are five flaps formed in FIG. 6c. In 6d each radial cut defines two flaps and so as to form six flaps formed.

Figure 7A:
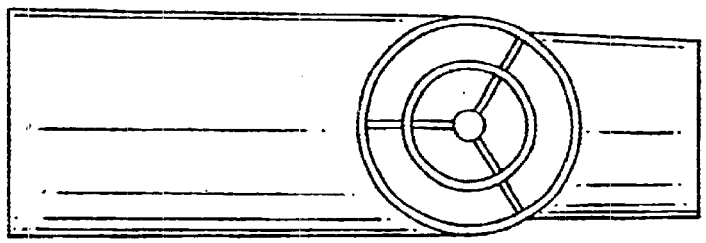
Figure 7B:
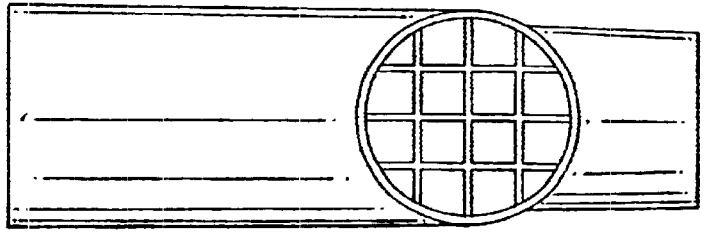

FIGS. 7a, 7b are plan views of alternative support means integral with the hollow mouthpiece element positioned so as to prevent the opening of the exhaust valve element during patient or user inhalation.

Figure 8:
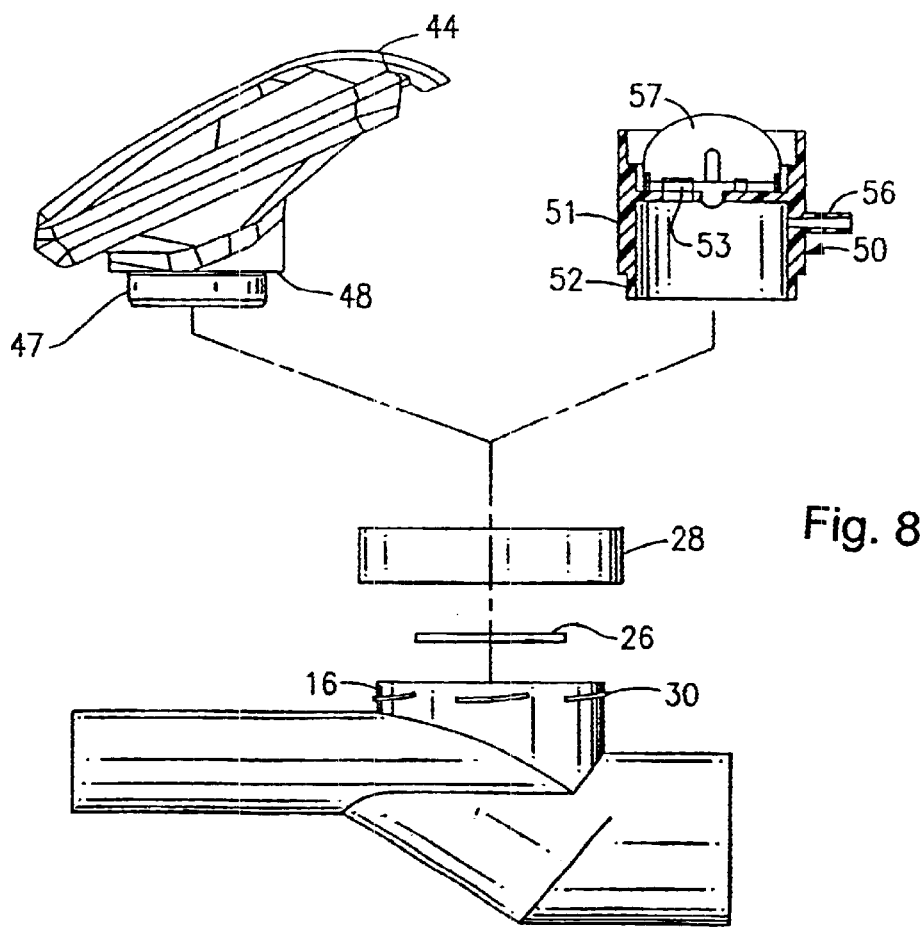
Figure 9:
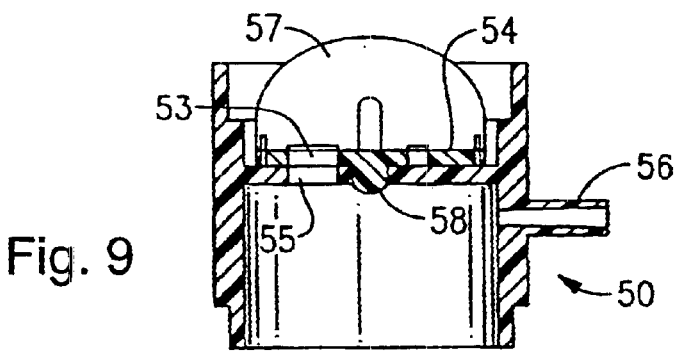
Figure 10:
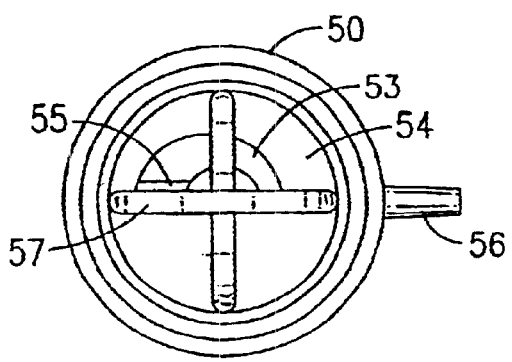
Figure 20:
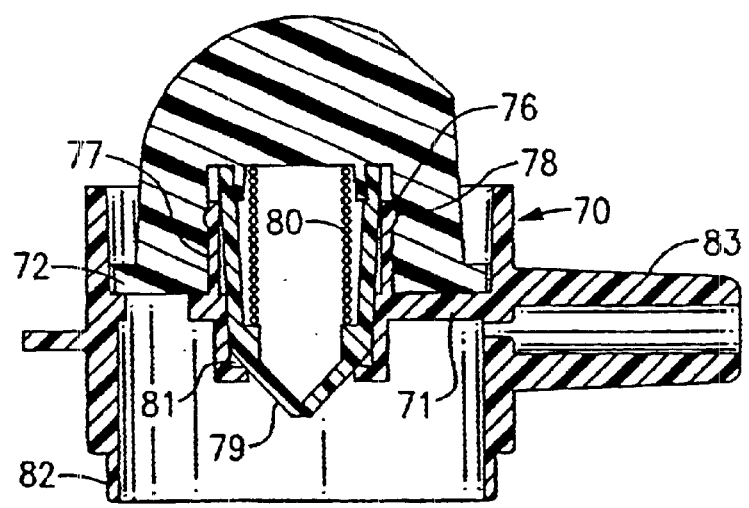
FIGS. 19 and 20 are respectively an exploded view and a cross-sectional elevation of a different embodiment of a PEP valve.
Figure 11:
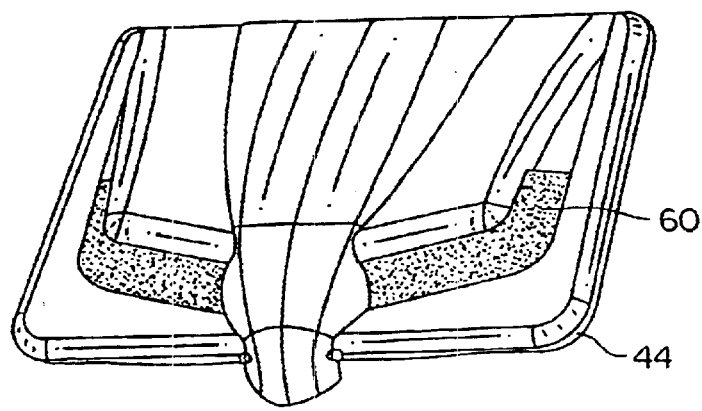
Figure 12:
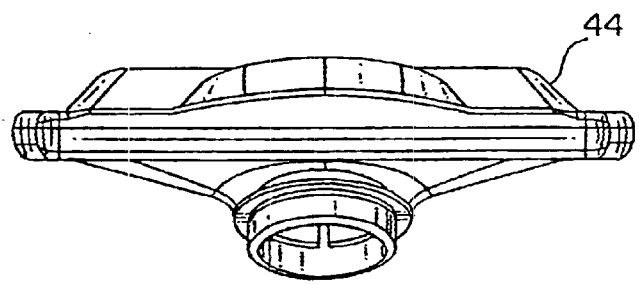
Figure 13:
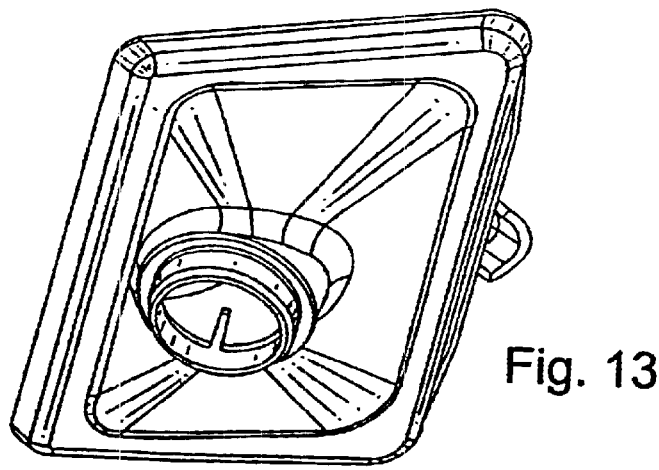
Figure 14:
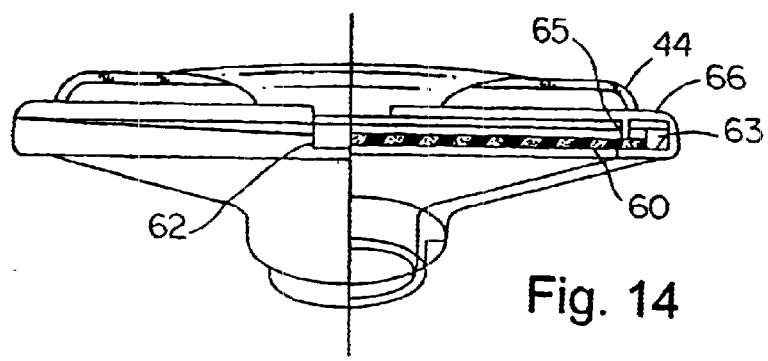
Figure 15:
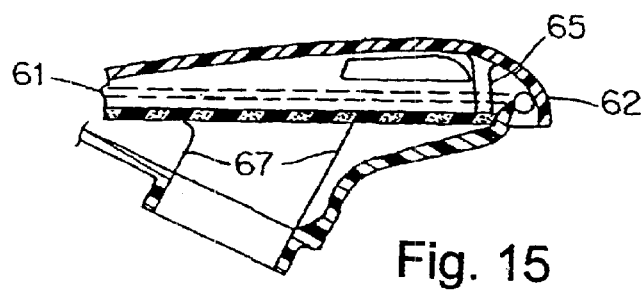
FIG. 15 is a cross-sectional side elevation of the filter body with the filter in place.
Figure 16:
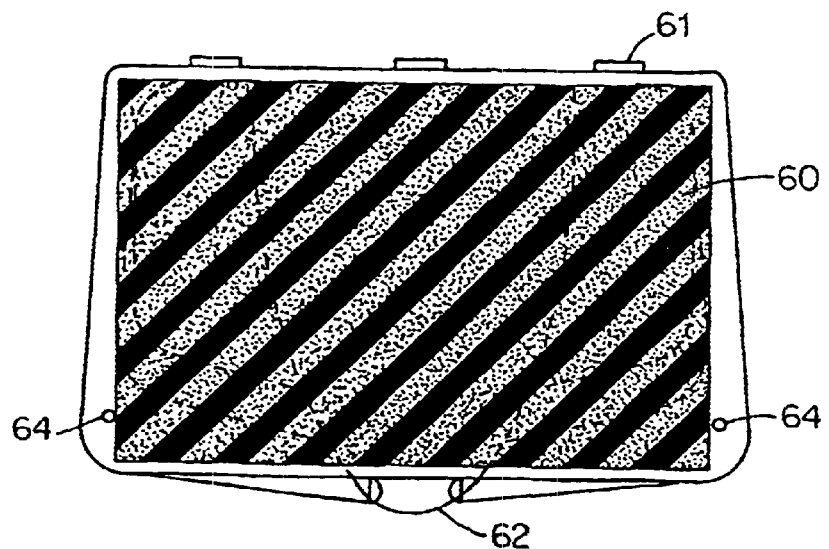
FIG. 16 is a top view of the lower portion of the filter body with the filter shown hatched.
Figure 17A:
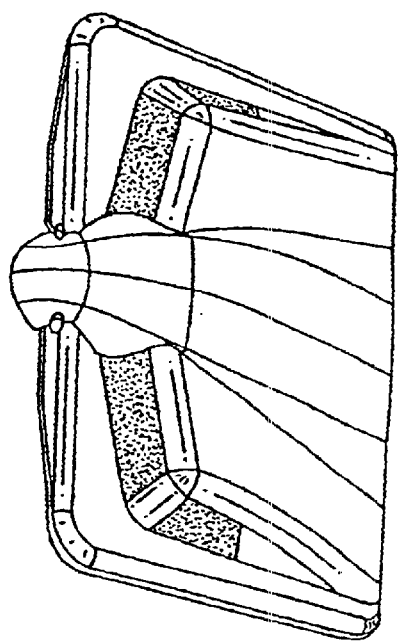
FIGS. 17A and 17B are two perspective views of another embodiment of the filter housing.
Figure 17B:
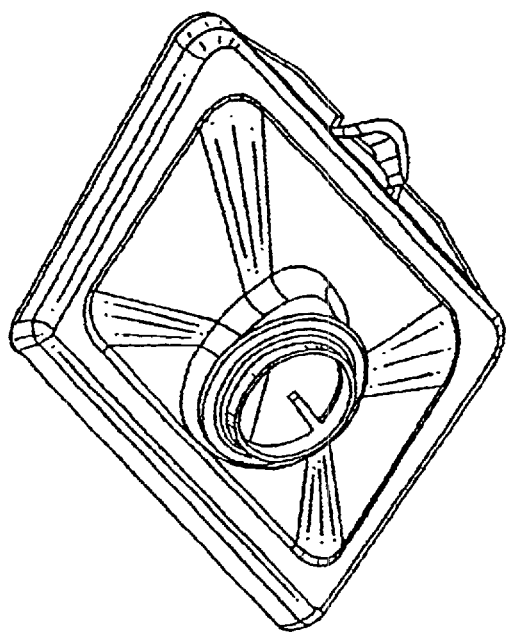
Figure 18A:
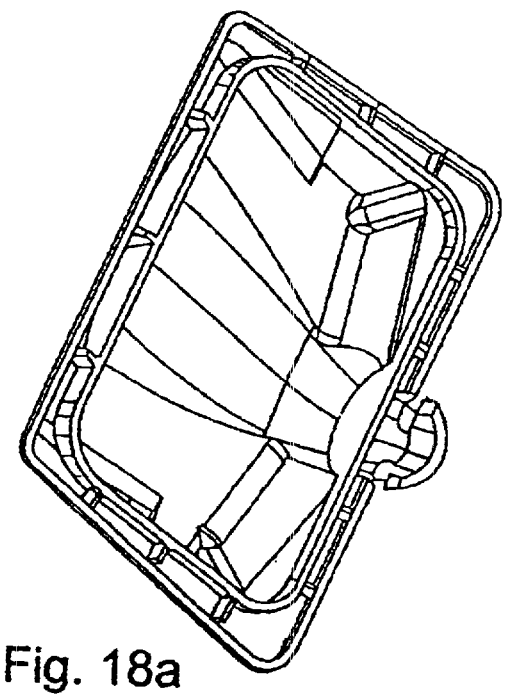
FIGS. 18A and 18B are two perspective views of the interiors of the top and bottom of the embodiment shown in FIG. 17.
Figure 18B:
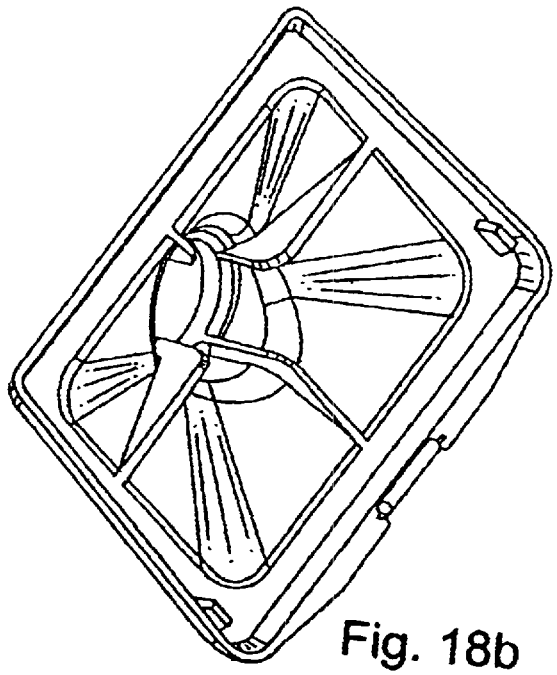
Figure 19:
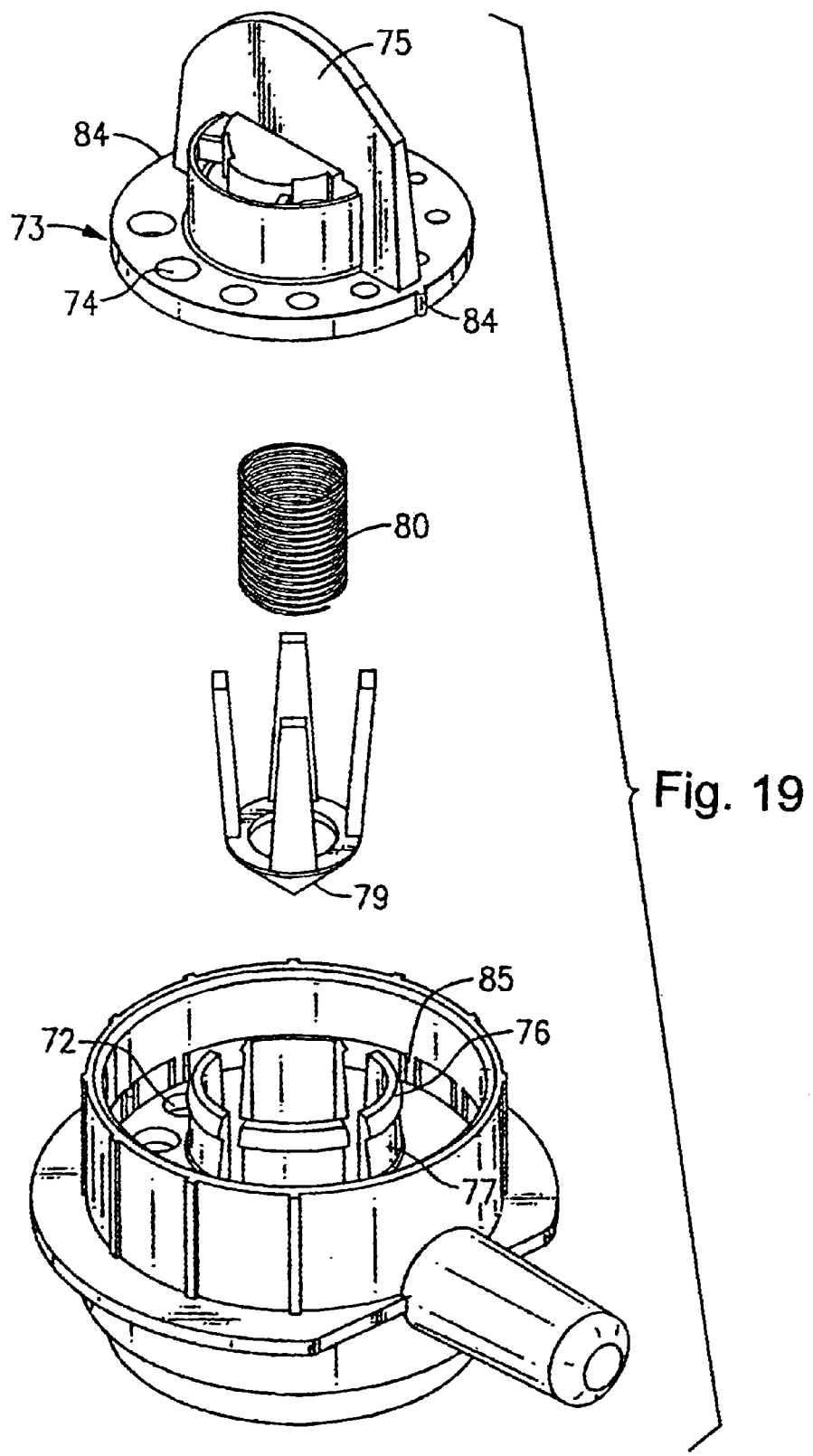

Referring to FIG. 8, the valve body 16 is provided with interrupted threads 30 evenly spaced around the outer circumference of the valve body to engage protrusion receiving internal threads (not shown) in the retaining ring 28. A filter body 44 is shown as being configured with a cylindrical base member 47 which is sized to be snugly fit into the interior of the retaining ring 28.

The cylindrical base 47 extends below the filter body a distance that is less than the distance from the top of the retaining ring 28 to the flexible valve. In this manner, the filter body will be sized to be snugly received in the retaining ring which will abut the surface 48 without the cylindrical base touching or otherwise interfering with the function of the one-way valve element (valve disc 26). Optionally, a positive expiratory pressure (PEP) valve 50 having a body 51 configured with a base member 52 which is sized to be received in the retaining ring 28 with a snug fit is provided which will enable the mouthpiece to be used as described in U.S. Pat. No. 5,584,285 as either a PEP device or as a part of the breathing circuit described therein with a filter to reduce exposure to excess aerosol medication. This is an important use to reduce health care provider exposure to patient contaminating aerosol or highly toxic medicants.

The PEP valve 50, which will be described more fully hereinafter, is provided with the feature of adjustable back pressure which can be used to aid in the deposition and prevent the loss of aerosol in the lungs by creating airflow conditions which are more controlled and thereby permit deeper deposits which are less susceptible to mucocillary removal. Such devices also help improve patient compliance with proper breathing techniques and helps to strengthen the muscles of respiration. This can be accomplished by providing either inhalation resistance, exhalation resistance or both. Further, the incorporation of the variable resistance valve combines maximum aerosol density and respiration of optimum particle size for many treatment options including antibiotics, antivirals, enzymes, bio-reactive substances and genetic therapies.

The PEP valve 50 has a variable cross-section semicircular slot 53 (FIG. 10) on a rotationally movable plate 54 can be adjusted to present the capability of providing for variable back pressure provided by an adjustably sized outlet for the opening 55 which communicates with the interior of the PEP body 51. The back pressure may be measured, if clinically desired, by a manometer fitted to the nipple 56 during treatment or exercise. A handle 57 is integral with the plate 54 which is rotatably captive in the PEP body 51 by means of a rivet or pivot 58. The components are sized to prevent significant leakage which could alter the value of the manometer readings.

In operation the mouthpiece, the PEP valve may be incorporated into a breathing circuit with or without the one way valve disc and filter 44, or a pressurized external gas source can be used for various therapies and exercises. Such a device, which can be called a positive airway pressure adjunct and can be used in modified circuits to mobilize secretions, treat atelectasis and provide continuous positive airway pressure (CPAP), positive expiratory pressure (PEP), and expiratory positive airway pressure (EPAP) therapies.

During CPAP therapy, the patient breathes from a pressurized circuit against a threshold resistor (water-column, weighted, or spring loaded) that maintains consistent preset airway pressures from 5 to 20 cm $H_2O$ during both inspiration and expiration. By strict definition, CPAP is any level of above-atmospheric pressure. CPAP requires a gas flow to the airway during inspiration that is sufficient to maintain the desired positive airway pressure.

During PEP therapy, the patient exhales against a fixed-orifice resistor, generating pressures during expiration that usually range from 10 to 20 cm $H_2O$. PEP does not require a pressurized external gas source.

During EPAP therapy the patient exhales against a threshold resistor, generating preset pressures of 10 to 20 cm $H_2O$. EPAP does not require a pressurized external gas source.

The device described herein is suited for PEP therapy in the configurations shown.

The size of the device provides both convenience comfort and greater independence for the patient during treatment.

Referring now to FIGS. 11, 12, 13, 14, 15 and 16, a filter housing 44 is provided which will fit into the retaining ring 28 as previously described. A filter element 60 is received in the housing 44 which is hinged at the back 61 and closed at the front with a suitable latch structure 62. The interior of the filter housing 44 is provided with a peripheral apron 63 and locator pins 64 which, in combination with the structure of the rear of the housing locates the filter element 60 on the apron (as shown in FIG. 14). Clamping protrusions 65 molded into the lid 66 of the filter housing 44 are sized to firmly squeeze the edge of the filter element 60 onto the apron 63 to seal and prevent lateral movement of the element during use. Ribs 67 are provided as projections from the cylindrical base 47 to provide central support for the filter element to minimize sagging. The filter element itself is selected to provide a significant reduction in visible particles, a 3M product 0.3 micron Filtrate filter being preferred. In the configuration shown the effective area of the filter exposed to patient exhalation is nominally a surface measuring about 5 cm by about 7.5 cm (i.e. about 37.5 $cm^2$). In order to be most effective, the inlet and exhaust areas of the filter housing should be comparable in cross-sectional area. The textured outlet areas shown in FIG. 11 on the top surfaces of the housing 44 are therefore sized to be substantially the same in effective exhaust area as the inlet cross-sectional area.

In one arrangement the filter housing may be attached to the retaining ring by way of the PEP valve.

An alternative construction for the PEP valve will now be described with reference to FIGS. 19 and 20. A cylindrical body 70 has an integral annular flange 71 defining an annular array of three evenly spaced openings 72 defining a passageway through the valve under the control of a rotatable valve member 73 which defines an annular array of openings 74 of the same spacing as openings 72 and having a range of different sizes. The member 73 is rotatable by a handle 75, integral therewith, relative to the openings 72 to adjust the size of the passageway. The valve member 73 is captively mounted to the body 70 by detents 76 formed on an exterior cylindrical surface of a hollow boss 77 integral with and forming a central opening in the flange 71. The boss 77 defines a plurality of axially extending slots to provide for assembly as the detents are inserted in a bore of the valve member 73 for engagement with recesses 78 therein. Valve member locating detents 84 resiliently retain the valve member 73 relative to body recesses 85 to retain desired alignment of openings 72 and 74.

A poppet valve member 79 is located in the central opening in the flange 71 and seats under the bias of a spring 80 against a valve seat 81. The poppet valve member 79 includes a guide spider 82 about the spring 80 which is guided by a spider guide opening in the boss 77 to control alignment of the poppet valve member 79 with the valve seat 81.

In similar fashion to the PEP valve described with reference to FIGS. 8, 9 and 10, the body 70 defines a base member 82 to be received in the retaining ring 28 and nipple 83 for attachment to a manometer to measure back pressure, if desired.

In use, the passageway is adjusted to desired cross-sectional area by rotation of the valve member 73. During exhalation, if the back pressure in the body 70 below the poppet valve exceeds the bias of spring 80, the poppet valve member 79 lifts from the valve seat overcoming the spring bias to relieve the back pressure by allowing exhaled gas to bypass the passageway.

The PEP valve of this invention has a controllable exhalation resistance of from 5–20 cm. $H_2O$ (water pressure) at flow rates of 10–55 liters/minute. The pressure relief poppet valve is spring biased to insure that flow resistance values over 20 cm. $H_2O$ are actively vented.

What is claimed is:

1. A mouthpiece device for inspiration of a mist from a nebulizer comprising:

an inlet connector adapted to engage the outlet port of a nebulizer; a hollow mouthpiece element for insertion into a patient's mouth, a conduit forming a fluid connection between the inlet connector and the hollow mouthpiece element; an exhaust outlet for removing exhalation gases which are exhaled into the mouthpiece element to outside the device, said exhaust outlet being positioned on the conduit between the inlet connector and the mouthpiece element; and a filter housing incorporating a filter to filter exhaled gases passing from the exhaust outlet, wherein a variable resistance orifice housing having an fixed size inlet and a variable sized exhaust opening is mounted to the mouthpiece element for variable resistance fluid communication between the interior of said hollow mouthpiece through the variable sized exhaust opening, said variable resistance to fluid flow being provided by an arcuate shaped opening of varying cross-section provided in a plate which is slidably received in contact with a fixed cross-section opening to the inlet side of the housing, a handle being affixed to the plate to move the arcuate opening over the fixed cross-section opening to control resistance to the fluid flow between the inlet and the exhaust openings.

2. A mouthpiece device for inspiration of a mist from a nebulizer comprising:

an inlet connector adapted to engage the outlet port of a nebulizer; a hollow mouthpiece element for insertion into a patient's mouth, a conduit forming a fluid connection between the inlet connector and the hollow mouthpiece element; an exhaust outlet for removing exhalation gases which are exhaled into the mouthpiece element to outside the device, said exhaust outlet being positioned on the conduit between the inlet connector and the mouthpiece element; and a filter housing incorporating a filter to filter exhaled gases passing from the exhaust outlet, wherein a positive expiratory pressure valve comprises a variable resistance orifice housing having a fixed size opening and a variable sized exhaust opening is mounted to the mouthpiece element for variable resistance fluid communication between the interior of said hollow mouthpiece through the variable sized exhaust opening, said variable resistance to fluid flow being provided by an arcuate array of openings of varying cross-section provided in a plate which is slidably received in contact with a fixed size opening to the inlet side of the housing, a handle being affixed to the plate to move the arcuate opening over the fixed cross-section opening to control resistance to the fluid flow between the inlet and the exhaust openings.

3. The mouthpiece device according claim 2, wherein the fixed size opening comprises an annular array of equally sized evenly spaced openings having the same annular spacing as the arcuate array of openings.

4. The mouthpiece device according to claim 2, wherein the positive expiratory pressure valve has a resiliently biased pressure relief valve arranged to open when the back pressure of the exhaled gases resulting from operation of the positive expiratory pressure valve exceeds a desired pressure to relieve that back pressure.

* * * * *